(12) United States Patent
Consoli et al.

(10) Patent No.: US 11,497,698 B2
(45) Date of Patent: Nov. 15, 2022

(54) HAIR COLOURING COMPOSITIONS

(71) Applicant: BEAUTY & BUSINESS S.p.A., Milan (IT)

(72) Inventors: Antonio Consoli, Urgnano (IT); Massimo Fabbi, Mozzo (IT); Katiuscia Grevalcuore, Bergamo (IT); Emanuela Facchetti, Romano di Lombardia (IT)

(73) Assignee: BEAUTY & BUSINESS S.p.A., Milan (IT)

( * ) Notice: Subject to any disclaimer, the term of this patent is extended or adjusted under 35 U.S.C. 154(b) by 0 days.

(21) Appl. No.: 17/392,812

(22) Filed: Aug. 3, 2021

(65) Prior Publication Data
US 2022/0040073 A1 Feb. 10, 2022

(30) Foreign Application Priority Data

Aug. 7, 2020 (IT) .......................... 102020000019576

(51) Int. Cl.
*A61Q 5/10* (2006.01)
*A61K 8/44* (2006.01)
*A61K 8/22* (2006.01)

(52) U.S. Cl.
CPC ................ *A61K 8/442* (2013.01); *A61K 8/22* (2013.01); *A61K 8/44* (2013.01); *A61Q 5/10* (2013.01); *A61K 2800/30* (2013.01); *A61K 2800/4324* (2013.01); *A61K 2800/882* (2013.01)

(58) Field of Classification Search
CPC . A61Q 5/10; A61K 8/22; A61K 8/411; A61K 8/4926; A61K 8/415; A61K 2800/4324; A61K 8/41; A61K 2800/882; A61K 8/442; A61K 8/44; A61K 2800/30
USPC ............................................................ 8/405
See application file for complete search history.

(56) References Cited

U.S. PATENT DOCUMENTS 4,447,366 A * 5/1984 Morelle .................... A61P 3/00
554/59

FOREIGN PATENT DOCUMENTS

IT     201700118597 A1     4/2019

OTHER PUBLICATIONS

Search Report and Written Opinion of Priority Document IT 202000019576 dated Apr. 26, 2021.

* cited by examiner

*Primary Examiner* — Eisa B Elhilo
(74) *Attorney, Agent, or Firm* — Silvia Salvadori, P.C.; Silvia Salvadori

(57) ABSTRACT

Disclosed is a hair colouring composition containing amino acids with at least a pKa greater than 10, oxidative dyes, and acetylaspartic acid or salts thereof. The compositions according to the invention do not contain ammonia or ethanolamine, do not damage the hair, guarantee shine and combability, and also cover white hair and withstand blue light.

9 Claims, No Drawings

HAIR COLOURING COMPOSITIONS

This non-provisional application claims priority to and the benefit of Italian Application No. 102020000019576 filed 7 Aug. 2020, the content of which is incorporated herein by reference in its entirety.

The invention relates to hair colouring compositions comprising amino acids with a pKa greater than 10, oxidative dyes, and acetylaspartic acid or salts thereof, in the absence of ammonia and ethanolamine.

PRIOR ART

Oxidative dyes have become very important in the hair colouring industry because they lighten the natural colour of the keratin fibre, allowing a radical change in hair colour in line with current fashions; oxidative preparations also cover white hair. Oxidative dyes are created by reacting primary intermediates and couplers in the presence of an oxidant, to produce a wide range of shades. The dyes thus obtained must have excellent properties in terms of resistance to washing, permanent wave treatments, acids, bases, abrasion, sunlight, and artificial light generated by LEDs and devices such as computers and smartphones (blue light). They are currently stable for four to six weeks under normal conditions, and are therefore called "permanent" dyes.

The oxidative system is based on the reaction of primary intermediates with couplers; both types of molecule are colourless. In the presence of air or oxidants such as hydrogen peroxide, primary dyes, which are primary aromatic amines with a hydroxyl or additional amino group, substituted or not substituted, in the para or ortho position, react with couplers such as resorcinol, m-aminophenol, m-phenylenediamine, 1-naphthol and pyridine As the dye molecules thus formed in the cuticle are larger than the starting primary intermediates and the highly diffusible couplers, they remain trapped, and there is therefore no significant fading due to successive washes or the action of external agents.

Oxidative dyes also require the presence of an alkalising agent. Ammonia is the most commonly used alkalising agent, despite its unpleasant pungent odour.

In the last 20 years, ammonia-free hair colouring preparations containing alkanolamines, in particular monoethanolamine (MEA), have become widespread on the market. Alkanolamines are known to be particularly aggressive to the capillary fibre because they tend to damage the hair structure, leading to loss of shine, combability and elasticity (Comparison of damage to human hair fibers caused by monoethanolamine- and ammonia-based hair colorants, J. Cosmet. Sci., 65, 1-9; WO2017109132).

Patent IT201700118597 describes a hair colouring composition based on oxidative dyes containing, as7 sole alkalising agent, an amino acid with a pKa greater than 10.00 (preferably arginine and lysine) combined with a fatty acid ester with glycerol polyethoxylate.

Said composition does not have an unpleasant odour, nor does it damage the capillary fibre; on the contrary, it guarantees excellent results in terms of shine, combability and elasticity.

However, said composition is unable to cover white hair adequately, a performance which is in great demand from users of hair colouring preparations, and the colour is not blue-light-stable, but tends to change with time due to lengthy, repeated exposure. Moreover, the composition described in IT201700118597 is characterised in that the mixture (dye+activator) tends to darken rapidly. As well as being an aspect disliked by hairdressers for aesthetic reasons, this characteristic indicates premature oxidation of the dyes, with consequent loss of performance of the product in terms of colouring/coverage of white hair.

The purpose of the present invention is therefore to provide a hair colouring composition which does not have an unpleasant odour, does not damage the hair, and guarantees cosmetic properties such as shine and combability but also covers white hair better and withstands blue light.

DESCRIPTION OF THE INVENTION

It has now been found that said purposes are achieved with a composition containing:
i) an alkalising agent consisting of at least one amino acid with at least a pKa greater than 10;
ii) at least one oxidative dye comprising a primary dye and a coupler;
iii) acetylaspartic acid or salts thereof.

The compositions according to the invention contain neither ammonia nor ethanolamine Said composition, optionally mixed at a suitable dilution with an activator, permanently dyes the hair, allowing the natural hair to be lightened and white hair to be covered.

The composition according to the invention can take the form of an O/W (oil-in-water) or W/O (water-in-oil) emulsion, a liquid, biphasic liquid, gel, oil, aerosol or mousse, or can be in solid form.

The composition according to the invention can be in "ready-to-use" form, comprising two or more ingredients designed to be mixed before use. Alternatively, it can be applied directly to the hair. In that event the activator is the oxygen present in the air.

The amino acid with a pKa greater than 10.00 can be any amino acid in form L or D having a pKa greater than 10.00.

Examples of amino acids with a pKa greater than 10.00 include arginine, lysine and proline. The preferred amino acids are arginine and lysine. The amount of amino acid can typically range from 0.1 to 20%, preferably 0.2 to 10%, of the total weight of the composition.

Acetylaspartic acid is present in amounts ranging from 0.001 to 3% of the total weight of the composition.

The oxidative dye is preferably selected from:
1-Acetoxy-2-Methylnaphthalene, 5-Amino-4-Chloro-o-Cresol, 4-Amino-m-Cresol, 6-Amino-m-Cresol, 3-Amino-2,4-Dichlorophenol, 6-Amino-2,4-Dichloro-m-Cresol, 3-Amino-2,4-Dichlorophenol, 5-Amino-2, 6-Dimethoxy-3-Hydroxypyridine, 5-Amino-2,6-Dimethoxy-3-Hydroxypyridine, 3-Amino-2,6-Dimethylphenol, 2-Amino-5-Ethylphenol, 5-Amino-4-Fluoro-2-Methylphenol Sulphate, 2-Amino-4-Hydroxyethylaminoanisole, 2-Amino-4-Hydroxyethylaminoanisole, 2-Amino-3-Hydroxypyridine, 4-Amino-2-Hydroxytoluene, 2-Aminomethyl-p-Aminophenol, 4-Amino-2-Nitrodiphenylamine-2'-Carboxylic Acid, m-Aminophenol, o-Aminophenol, p-Aminophenol, 1,3-Bis-(2,4-Diaminophenoxy)propane, 4,6-Bis(2-Hydroxyethoxy)-m-Phenylenediamine, 2,6-Bis(2-Hydroxyethoxy)-3,5-Pyridinediamine, N,N-Bis(2-Hydroxyethyl)-p-Phenylenediamine, 4-Chloro-2-Aminophenol, 2-Chloro-p-Phenylenediamine, 4-Chlororesorcinol, N-Cyclopentyl-m-Aminophenol, 3,4-Diaminobenzoic Acid, 4,5 -Diamino-1-((4-Chlorophenyl)Methyl)-1H-Pyrazole-Sulphate, 2,3-Diaminodihydropyrazolo Pyrazolone Dimethosulphonate, 2,4-Diaminodiphenylamine, 4,4'-Diaminodiphenylamine, 2,4-Diamino-5-Methylphenetole, 2,-Diamino-5-Methylphenoxyethanol, 4,5-Diamino-1-Methylpyrazole, 2,4-Diaminophenol, 2,4-Diaminophenoxyethanol, 2,6-Diaminopyridine, 2,6-Diamino-3-((Pyridin-3-yl)Azo)Pyridine, N,N-Diethyl-m-Aminophenol, N,N-Diethyl-p-Phenylenediamine, N,N-Diethyltoluene-2,5-Diamine, 2,6-Dihydroxy-3,4-Dimethylpyridine, 2,6-Dihydroxyethylaminotoluene, Dihydroxyindole, Dihydroxyindoline, 2,6-Dimethoxy-3,5-Pyridinediamine, m-Dimethylaminophenyl Urea, N,N-Dimethyl-p-Phenylenediamine, 2,6-Dimethyl-p-Phenylenediamine, N,N-Dimethyl 2,6-Pyridinediamine, 4-Ethoxy-m-Phenylenediamine, 3-Ethylamino-p-Cresol, 4-Fluoro-6-Methyl-m-Phenylenediamine, 1-Hexyl 4,5-Diamino Pyrazole Sulphate, Hydroquinone, Hydroxyanthraquinoneaminopropyl Methyl Morpholinium Methosulphate, Hydroxybenzomorpholine, Hydroxyethoxy Aminopyrazolopyridine, Hydroxyethylaminomethyl-p-Aminophenol, 1-Hydroxyethyl 4,5-Diamino Pyrazole, Hydroxyethyl-2,6-Dinitro-p-Anisidine, Hydroxyethyl-3,4-Methylenedioxyaniline, Hydroxyethyl-p-Phenylenediamine, 2-Hydroxyethyl Picramic Acid, 6-Hydroxyindole, Hydroxypropyl Bis(N-Hydroxyethyl-p-Phenylenediamine), Hydroxypropyl-p-Phenylenediamine, Hydroxypyridinone, Isatin, N-Isopropyl 4,5-Diamino Pyrazole, N-Methoxyethyl-p-Phenylenediamine, 6-Methoxy-2-methylamino-3-aminopyridine, 2-Methoxymethyl-p-Aminophenol, 2-Methoxyethyl-p-Phenylenediamine, 2-Methoxy-p-Phenylenediamine, 6-Methoxy-2,3-Pyridinediamine, 4-Methoxytoluene-2,5-Diamine, p-Methylaminophenol, 4-Methylbenzyl 4,5-Diamino Pyrazole, 2,2'-Methylenebis 4-Aminophenol, 3,4-Methylenedioxyaniline, 3,4-Methylenedioxyphenol, 2-Methyl-5-Hydroxyethylaminophenol, Methylimidazoliumpropyl p-Phenylenediamine, 2-Methyl-1-Naphthol, 2-Methylresorcinol, 1,5-Naphthalenediol, 1,7-Naphthalenediol, 2,3-Naphthalenediol, 2,7-Naphthalenediol, 1-Naphthol, 2-Naphthol, PEG-3 2,2'-Di-p-Phenylenediamine, p-Phenetidine, m-Phenylenediamine, p-Phenylenediamine, Phenyl Methyl Pyrazolone, N-Phenyl-p-Phenylenediamine, Picramic Acid, Pyrocatechol, Pyrogallol, Resorcinol, Sodium Picramate, Tetraaminopyrimidine, Tetrahydro-6-Nitroquinoxaline, Tetrahydropyranyl, Resorcinol, Toluene-2,5-Diamine, Toluene-2,6-Diamine, Toluene-3,4-Diamine, 2,5,6-Triamino-4-Pyrimidinol, 1,2,4-Trihydroxybenzene. The oxidative dyes can be in the form of salts.

The total amount of the combination of primary dyes and couplers preferably ranges between about 0.001 and 20% by weight, more preferably between about 0.002 and 10% by weight, and even more preferably between about 0.01 and 6.0% by weight.

As stated, the hair colouring preparation according to the invention can be applied directly to the hair, colouring it due to the presence of oxygen in the air, or can be mixed with an activator. In the context of the invention, "activator" means an agent able to promote the oxidation and coupling reaction between primary dyes and couplers.

"Activator" means hydrogen peroxide, carbamide peroxide, perborates and persulphates or peracids. Hydrogen peroxide is preferred. The amount of activator, if present, can range from 0.1 to 50% by weight of the ready-to-use mixture.

When the dye is mixed with the activator, which in most cases is acidic (pH about 2 to 6.5), the pH of the ready-to-use hair colouring preparations according to the invention acquires a value determined by the amount of alkalising agent and the amount of acid in the oxidant, and by the mixing ratio. Depending on their composition, the ready-to-use hair colouring preparations thus obtained can be weakly acidic, neutral or alkaline, with a pH ranging from about 3 to 11, preferably from 6.5 to 11. In the context of the invention, "alkalising agent" or "alkaliser" means an ingredient or combination of ingredients able to adjust the pH of the cosmetic composition to a value above 7.

The dye can also contain a neutraliser. In the context of the invention, "neutralising agent" or "neutraliser" means an ingredient able to adjust the pH of the composition from a value of less than 7 to a neutral pH.

Examples of neutralisers are sodium hydroxide, potassium hydroxide, urea, allantoin, tripotassium phosphate, sodium saccharine, and combinations thereof. The neutralising agents are present in amounts such as to neutralise the acid ingredients present in the formulation.

The hair colouring preparations according to the invention can also contain one or more additives commonly used in the cosmetic industry for solutions, creams, emulsions, gels, aerosols, foams, powders and granulates. Examples of said additives include solvents, emulsifiers, wetting agents, surfactants, thickeners, conditioners and auxiliaries.

Examples of solvents include water, low-molecular-weight aliphatic mono- or polyalcohols and esters and ethers thereof, in particular alkanols having 1 to 4 carbon atoms, such as ethanol, n-propanol, isopropanol, butanol and isobutanol; bivalent or trivalent alcohols, in particular having 2 to 6 carbon atoms, such as ethylene glycol, propylene glycol, 1,3-propanediol, 1,4-butanediol, 1,5-pentanediol, 1,6-hexanediol, 1,2,6-hexanetriol, glycerin, diethylene glycol, dipropylene glycol, polyalkylene glycols, such as triethylene glycol, polyethylene glycol, tripropylene glycol and polypropylene glycol; low-molecular-weight alkyl ethers of multivalent alcohols, such as ethylene glycol monomethyl ether, ethylene glycol monoethyl ether, ethylene glycol monopropyl ether or ethylene glycol monobutyl ether, diethylene glycol monomethyl ether or diethylene glycol monoethyl ether, triethylene glycol monomethyl ether or triethylene glycol monoethyl ether; ketones and keto alcohols, in particular having 3 to 7 carbon atoms, such as acetone, methyl ethyl ketone, diethyl ketone, methyl isobutyl ketone, methyl phenyl ketone, cyclopentanone, cyclohexanone and diacetone alcohol; ethers such as dibutyl ether, tetrahydrofuran, dioxane or diisopropylether; esters such as ethyl formate, methyl formate, methyl acetate, ethyl acetate, propyl acetate, butyl acetate, phenyl acetate, ethylene glycol monoethyl ether acetate or acetic acid hydroxyethyl ester; amides such as N-methylpyrrolidone; urea, tetramethyl urea and thiodiglycol. The emulsifiers can be anionic, cationic, non-ionic, amphoteric or zwitterionic.

Examples of surfactants include fatty alcohol sulphates, alkylsulphonates, alkylbenzene sulphonates, alkyltrimethyl ammonium salts, alkylbetaine, α-olefin sulphonates, ethoxylated fatty alcohols, ethoxylated nonylphenols, fatty acid alkanolamides, ethoxylated esters of fatty acids, polyglycol ether sulphates of fatty acids and alkyl polyglucosides.

Examples of thickeners include higher fatty alcohols, starches, cellulose derivatives, vaseline, paraffin oil, fatty acids and other fatty components in emulsified form, water-soluble polymer thickeners, such as natural gums, guar gum, xanthan gum, carob flour, pectin, dextran, agar-agar, amylose, amylopectin, dextrin, synthetic clays or hydrocolloids, such as polyvinyl alcohol. Examples of conditioning agents include lanolin derivatives, cholesterol, pantothenic acid, water-soluble cationic polymers, protein derivatives, provitamins, vitamins, plant extracts, sugar and betaine.

Examples of auxiliary agents include electrolytes, antioxidants, fatty amides, sequestering agents, film-forming agents and preservatives, and beeswax.

It can be advantageous to add to the hair colouring preparations according to the invention non-ionic and/or anionic surfactants, such as fatty alcohol sulphates, in particular lauryl sulphate or sodium cocoyl sulphate; ethoxylated fatty alcohol sulphates, in particular sodium lauryl ether sulphates with 2 to 4 molecular units of ethylene oxide, ethoxylated esters of fatty acids, ethoxylated nonylphenols, ethoxylated fatty alcohols, alkylbenzene sulphonates or alkanolamides of fatty acids, in an amount preferably ranging from about 0.1 to 30% by weight, more preferably from 0.2 to 15% by weight.

Examples of cationic surfactants are quaternary ammonium compounds; ammonium halides such as alkyltrimethylammonium chlorides, dialkyldimethylammonium chlorides and trialkylmethylammonium chlorides. Specific examples are cetyltrimethylammonium chloride, stearyltrimethylammonium chloride, distearyldimethylammonium chloride, lauryldimethylammonium chloride, lauryldimethylbenzylammonium chloride, tricetylmethylammonium chloride and quaternised protein hydrolysates.

As well as non-ionic organic thickeners with properties similar to wax and non-ionic surfactants, the dye can include the usual cosmetic cationic resins. Particularly preferred are Polyquaternium-6 (poly(dimethyl-diallylammonium chloride)), Polyquaternium-7 (diethyldiallylammonium chloride/acrylamide copolymer), Polyquaternium-10 (cationic cellulose), Polyquatenium-11 (N,N-dimethylaminoethylmethacrylic acid/PVP copolymer diethyl sulphate), Polyquaternium-22, Polyquaternium-35 and Polyquaternium-37 (trimethylaminoethyl methacrylate chloride polymer), either alone or in mixtures thereof. The total amount of said cationic resins in the preparation can range from about 0.1 to 6% by weight.

The composition according to the invention can be applied to the hair by the following methods:

1—The composition is mixed with an activator immediately before colouring the hair, and a sufficient amount of ready-to-use hair colouring mixture, generally about 60 to 200 grams, depending on the thickness and amount of the hair, is then applied to the hair.

The mixture is left on the hair for 5 to 60 minutes at the temperature of 5 to 50° C., preferably for 35 minutes at 30° C.; the hair is then rinsed with water and dried. If necessary, the hair is washed with shampoo after rinsing and optionally rinsed again with a weak organic acid, such as an aqueous solution of tartaric acid. The hair is then dried. 2—The hair colouring preparation is applied directly to the hair and left for 5 to 60 minutes at a temperature ranging from 5 to 50° C., preferably for 35 minutes at 30° C.; the hair is then rinsed with water and dried. The hair colouring preparation can be applied for several consecutive days until the desired colour depth is reached. In this case the oxygen in the air acts as activator (progressive dye).

3—The hair colouring preparation is applied directly to the hair and then dried without rinsing. The hair colouring preparation can be applied for several consecutive days until the desired depth is reached. In this case the oxygen in the air acts as activator (progressive dye).

The following examples further illustrate the invention.

EXAMPLES

The ingredients listed in the examples are named according to the INCI nomenclature (European Community Decision 2006/257/EC as amended—International Nomenclature of Cosmetic Ingredients).

Table 1 shows the formula of the activators used for the examples below. Formulas F1, F2, F3 and F4 represent the different strengths of the activators.

Compositions F5 and F7 are compositions according to the invention, whereas compositions F6 and F8 are comparative.

TABLE 1

| | Activators | | | |
|---|---|---|---|---|
| | F1 | F2 | F3 | F4 |
| Ingredients (INCI) | % | % | % | % |
| AQUA (WATER) | qs 100 | qs 100 | qs 100 | qs 100 |
| HYDROGEN PEROXIDE | 12 | 9 | 6 | 3 |
| CETEARYL ALCOHOL | 3 | 3 | 3 | 3 |
| CETEARETH-20 | 0.6 | 0.6 | 0.6 | 0.6 |
| PHOSPHORIC ACID | 0.1 | 0.1 | 0.1 | 0.1 |
| SODIUM STANNATE | 0.2 | 0.2 | 0.2 | 0.2 |
| SODIUM LAURETH SULPHATE | 0.1 | 0.1 | 0.1 | 0.1 |
| PROPYLENE GLYCOL | 0.1 | 0.1 | 0.1 | 0.1 |
| DISODIUM PYROPHOSPHATE | 0.1 | 0.1 | 0.1 | 0.1 |
| DIMETHICONE | 0.1 | 0.1 | 0.1 | 0.1 |
| PEG-40 CASTOR OIL | 0.1 | 0.1 | 0.1 | 0.1 |
| PENTASODIUM PENTETATE | 0.1 | 0.1 | 0.1 | 0.1 |
| ETIDRONIC ACID | 0.1 | 0.1 | 0.1 | 0.1 |
| C12-13 ALKYL LACTATE | 1 | 1 | 1 | 1 |

TABLE 2

| Hair colouring preparations in cream form | | | | |
|---|---|---|---|---|
| | F5* | F6 | F7* | F8 |
| INGREDIENTS (INCI) | % | % | % | % |
| AQUA (WATER) | q.s. to 100 | q.s. to 100 | q.s. to 100 | q.s. to 100 |
| DENATURED ALCOHOL | 12 | 12 | 12 | 12 |
| OLEIC ACID | 12 | 12 | 12 | 12 |
| PROPYLENE GLYCOL | 10 | 10 | 10 | 10 |
| LAURETH-2 | 8 | 8 | 8 | 8 |
| LAURETH-3 | 4 | 4 | 4 | 4 |
| OLEYL ALCOHOL | 3.5 | 3.5 | 3.5 | 3.5 |
| LYSINE | 5 | 5 | — | — |
| ARGININE | — | — | 9 | 9 |
| SODIUM LAURETH SULPHATE | 3 | 3 | 3 | 3 |
| POTASSIUM HYDROXIDE | 2 | 2 | 2 | 2 |
| ACETYL ASPARTIC ACID | 0.5 | — | 0.5 | — |
| PARFUM (FRAGRANCE) | 0.7 | 0.7 | 0.7 | 0.7 |
| PEG-90 GLYCERYL ISOSTEARATE | — | — | — | 2 |
| CETRIMONIUM CHLORIDE | 0.5 | 0.5 | 0.5 | 0.5 |
| P-PHENYLENEDIAMINE | 0.4 | 0.4 | 0.4 | 0.4 |

TABLE 2-continued

Hair colouring preparations in cream form

|  | F5* | F6 | F7* | F8 |
|---|---|---|---|---|
| ERYTHORBIC ACID | 0.4 | 0.4 | 0.4 | 0.4 |
| SODIUM SULPHITE | 0.4 | 0.4 | 0.4 | 0.4 |
| EDTA | 0.3 | 0.3 | 0.3 | 0.3 |
| RESORCINOL | 0.3 | 0.3 | 0.3 | 0.3 |
| 2-METHYLRESORCINOL | 0.126 | 0.126 | 0.126 | 0.126 |
| M-AMINOPHENOL | 0.076 | 0.076 | 0.076 | 0.076 |
| P-AMINOPHENOL | 0.0668 | 0.0668 | 0.0668 | 0.0668 |
| 2,4-DIAMINOPHENOXYETHANOL HCL | 0.018 | 0.018 | 0.018 | 0.018 |

TABLE 3

Example of hair colouring preparation according to the invention, in gel form.

|  | F9* |
|---|---|
| INGREDIENTS (INCI) | % |
| AQUA (WATER) | qs 100 |
| PROPYLENE GLYCOL | 7 |
| HYDROXYETHYLCELLULOSE | 2 |
| CARBOMER | 1 |
| ACRYLATES/METHACRYLAMIDE COPOLYMER | 0.3 |
| ACETYL ASPARTIC ACID | 0.3 |
| ARGININE | 4 |
| LYSINE | 5 |
| SODIUM HYDROXIDE | 1 |
| PARFUM (FRAGRANCE) | 0.6 |
| SODIUM SULPHITE | 0.5 |
| ERYTHORBIC ACID | 0.3 |
| EDTA | 0.2 |
| TOLUENE-2,5-DIAMINE SULPHATE | 2.14 |
| 4-CHLORORESORCINOL | 1.367 |
| P-AMINOPHENOL | 0.736 |
| M-AMINOPHENOL | 0.701 |
| 2,4-DIAMINOPHENOXYETHANOL HCL | 0.074 |
| 2-AMINO-3-HYDROXYPYRIDINE | 0.031 |

Example 1

Coverage Test

The coverage was evaluated using a novel method defined herein as the GREY HAIR COVERAGE EVALUATION, designed by the Applicant.

The test involves simulating in the laboratory what happens on the model's head when white hair is covered.

Said method is highly reproducible, cheaper than the classic test performed on models, and provides easily comparable numerical values.

The method was validated by comparing the results with those deriving from the traditional method (panel test).

Homogenised natural locks of 90% white hair are used to conduct the test.

The product is only applied at the root of the locks, and only applied once, pressing the product on without combing it through, to simulate application to the hair roots as on a model.

At the end of the processing time the locks are rinsed, dried and combed.

The locks are then positioned on a specific support to keep the fibres aligned, and images are then obtained with a Jiusion digital microscope.

The RGB histogram of the distribution of the various shades of grey, from White (255) to Black (0), in the images of the various treatments, can be extracted using Image J software.

In the 0 to 100 range, the colour number is extracted at the maximum distribution value. The greater the dominant black, expressed by lower numerical values, the greater the coverage.

Compositions F5*, F6, F7* and F8 were used, mixed with composition F2 at the ratio of 1:1.5, and applied to locks by the GREY HAIR COVERAGE EVALUATION method described above.

The colour development time was 25 minutes at a temperature of 30° C. The results are set out in Table 4.

TABLE 4

| Formula | Colour at Max Value range 0-100 (average 3 locks) |
|---|---|
| F5* | 53 |
| F6 | 59 |
| F7* | 51 |
| F8 | 58.33 |

As will be seen, the treatments according to the invention have lower values, and the coverage of white hair is therefore greater. The difference in colour numbers between the compositions according to the invention and the comparators is significant in relation to the intrinsic limits of the technology (demi-permanent dyeing).

To confirm said data, formulas F5*, F6, F7*, F8 were each applied to 3 models with a percentage of white hair exceeding 70%.

5 industry experts were asked to allocate a score of 0 to 2, wherein 0 indicates no coverage of white hair, 1 indicates partial coverage, and 2 total coverage. Table 5 shows the scores allocated.

TABLE 5

| Formula | CONCLUSION |
|---|---|
| F5* | 1.5 |
| F6 | 0.5 |
| F7* | 1.5 |
| F8 | 1 |

The formulas according to the invention are those which have the highest coverage value, confirming the instrumental coverage test.

Example 2

Blue Light Test

A Konica Minolta colorimeter was used to evaluate the resistance of the colour to blue light (HEV).

In the CIELAB colour space, $L^*$ indicates sheen and $a^*$ and $b^*$ are the colour coordinates. $a^*$ and $b^*$ indicate the colour directions: +a* is the direction of red, −a* is the direction of green, +b* is the direction of yellow and −b* is the direction of blue.

Differences in colour can be expressed by ΔE values, which are defined by the following equation:

$$\Delta E=[(\Delta L^*)2+(\Delta a^*)2+(\Delta b^*)2]1/2$$

The lower the value of ΔE, the lower the loss of colour after exposure to blue light will be.

Formulas F5*, F6 and F8, mixed with activator F4 at the dilution ratio of 1:2, were used for this test. The mixture was applied to bleached locks and 100% white homogenised natural locks, and left to act for 30 minutes. The locks were then rinsed, dried and measured with the colorimeter. The locks were then exposed to blue light for 3 weeks in a container, and measured again with the colorimeter. Table 6 shows the ΔE data obtained.

TABLE 6

| Formula | ΔE NATURAL LOCKS | ΔE BLEACHED LOCKS |
|---|---|---|
| F5* | 1.61 | 4.82 |
| F6 | 4.44 | 6.50 |
| F8 | 7.8 | 5.66 |

Formula F5* according to the invention is the most resistant to exposure to blue light, because it exhibits lower DE values.

Example 3

Cosmetic Effect Test

Formulas F5*, F6, F7* and F8, mixed with activator F3 at the dilution ratio of 1:1, were used for this test. The mixture was applied to 3 bleached locks, which are notoriously difficult to comb because they are damaged, and left to act for 30 minutes. The locks were then rinsed, dried and evaluated by experts (panel test).

5 industry experts were asked to evaluate the cosmetic effect on the locks (shine, combability), and allocate a score of 0 to 2.

Score 0 indicates poor cosmetic effect, 1 indicates fair cosmetic effect, and 2 good cosmetic effect. Table 7 shows the scores allocated.

TABLE 7

| Formula | CONCLUSION |
|---|---|
| F5* | 1 |
| F6 | 0.5 |
| F7* | 1 |
| F8 | 1.5 |

Formulas F5* and F7* according to the invention are comparable with formula F8. Replacing PEG-90 glyceryl triisostearate with acetylaspartic acid does not adversely affect the cosmetic effect.

Example 4

Cream Oxidation Study

Formulas F5* and F6, mixed with activator F1 at a dilution ratio of 1:1.5, were used for this example. The mixture was applied to a sheet of paper, and photos were taken every 5 minutes.

The RGB histogram of the shades of grey from 0 (Black) to 255 (White) was then extrapolated with Image J software. The mean colour distribution values are set out in Table 10. The higher the numerical value, the lower the oxidation of the cream, which appears whiter. The slower the oxidation, the easier it will be for uncoupled dyes to penetrate the keratin fibre in depth before oxidising and forming the colour, thereby covering white hair better. Table 8 shows the scores allocated.

TABLE 8

| FORMULA | 0 MINUTES | 5 MINUTES | 10 MINUTES | 15 MINUTES | 20 MINUTES |
|---|---|---|---|---|---|
| F5* | 200 | 190.83 | 177.19 | 169.96 | 147.37 |
| F6 | 185.47 | 185.58 | 163.003 | 149 | 137.97 |
| F8 | 182.95 | 183.34 | 154.14 | 140.93 | 146.45 |

The higher the value, the better the oxidation (lighter). As shown in the table, the mixture of the formula according to the invention exhibits slower oxidation.

The invention claimed is:
1. A hair colouring composition containing:
   i) an alkalising agent consisting of at least one amino acid with at least a pKa greater than 10;
   ii) at least one oxidative dye comprising a primary dye and a coupler;
   iii) acetylaspartic acid or salts thereof;
   characterised by the absence of ammonia and ethanolamine.
2. A composition according to claim 1 in the form of an oil-in-water or water-in-oil emulsion, or in liquid or biphasic liquid form, or in the form of a gel, oil, aerosol or mousse or in solid form.
3. A composition according to claim 1 in "ready to use" form, comprising two or more ingredients to be mixed before use or suitable for direct application to the hair.
4. A composition according to claim 1, wherein the amino acids with a pKa higher than 10.00 are selected from arginine, lysine and proline.
5. A composition according to claim 4 wherein the amino acids are arginine or lysine.
6. A composition according to claim 1 wherein the amount of amino acid ranges from 0.1 to 20% of the total weight of the composition.
7. A composition according to claim 1 wherein acetylaspartic acid is present in an amount ranging from 0.001 to 3% of the total weight of the composition.
8. A composition according to claim 1 further comprising an activator selected from hydrogen peroxide, carbamide peroxide, perborates, persulphates and peracids.
9. A composition according to claim 1 wherein the total amount of the combination of primary dyes and couplers ranges from 0.001 to 20% by weight.

* * * * *